United States Patent [19]

Imaeda

[11] Patent Number: 5,418,367
[45] Date of Patent: May 23, 1995

[54] METHOD AND DEVICE FOR ANALYZING SUBSTANCES CONTAINED IN AN AREA

[75] Inventor: Kiyohide Imaeda, Niwa, Japan

[73] Assignee: Kabushiki Kaisha Tokai-Rika-Denki-Seisakusho, Aichi, Japan

[21] Appl. No.: 108,744

[22] PCT Filed: Mar. 19, 1992

[86] PCT No.: PCT/JP92/00335
§ 371 Date: Sep. 3, 1993
§ 102(e) Date: Sep. 3, 1993

[87] PCT Pub. No.: WO92/16827
PCT Pub. Date: Oct. 1, 1992

[30] Foreign Application Priority Data
Mar. 19, 1991 [JP] Japan .................. 3-054757

[51] Int. Cl.$^6$ .............. G01N 21/27; G01N 21/35
[52] U.S. Cl. ............. 250/339.12; 250/339.01
[58] Field of Search ........... 250/339, 340, 341, 358.1, 250/339.01, 340, 341.1, 339.07, 339.09, 339.12

[56] References Cited

FOREIGN PATENT DOCUMENTS 53-52198 5/1978 Japan .
61-47522 3/1986 Japan .
1-232316 9/1989 Japan .

OTHER PUBLICATIONS

J. Duvernoy et al.; *Optics Communications*; "Karhunen–Loeve Analysis of Multispectral Data from Landscapes"; Jan., 1980; pp. 39–44.
S. Kawata et al.; *Optical Society of America*; "Component Analysis of Spatial and Spectral Patterns in Multispectral Images. I. Basis"; vol. 4, No. 11; Nov., 1987; pp. 2101–2106.
Sasaki et al.; *Optical Society of America*; "Component Pattern Separation of Unknown-Mixture Images by Double Eigenvector Analysis"; vol. 7, No. 3; Mar., 1990; pp. 513–516.
King et al.; *Nuclear Instruments and Methods in Physics Research*; "From Small–Area to Imaging Photoabsorbtion Spectroscopy"; 1990; pp. 19–25.
Gianelli et al.; *Analytical Chemistry*; "Multichannel Imaging Spectrophotometer for Direct Analysis of Mixtures on Thin–Layer Chromatography Plates" Oct., 1983, pp. 1858–1862.
M. Lee; *Proceedings of the International Geoscience and Remote Sensing Symposium; Remote Sensing: Moving Towards the 21st Century;* "Automatic Mineral Map Generation Procedure from Imaging Spectrometer Date"; vol. II; Aug., 1988, pp. 1055–1058.
P. Hannequin, et al.; *Optik*, "Application of Multivariate Statistical Analysis to Energetic Image Series"; vol. 81, No. 1; 1988; pp. 6–11.
C. Mailhes et al.; *Journal of Optics;* "Spectral Image Compression"; vol. 21, No. 3; 1990; pp. 121–132.

Primary Examiner—Paul M. Dzierzynski
Assistant Examiner—Richard Hanig
Attorney, Agent, or Firm—Oliff & Berridge

[57] ABSTRACT

An area to be analyzed is divided into a large number of small regions. Light is projected on each of the small regions, and data on the spectrums of the small regions are obtained. Plural principal components are extracted from the obtained data (step 208). The principal component marks of the respective plural components are computed for each of the small regions (step 212). It is determined whether the principal component scores of the respective small regions exceed a predetermined value or not, respectively. Then, the plural small regions are classified into a plurality of small region groups so that the small regions, whose principal component marks of specified principal components exceed a predetermined value, are included in an identical small region group (step 214). A representative small region (best point) of the representative principal component marks of the specified principal component is extracted from each of the small region groups (step 224). Based on the spectrum of the representative small region, the substances constituting the small region groups are analyzed.

6 Claims, 7 Drawing Sheets

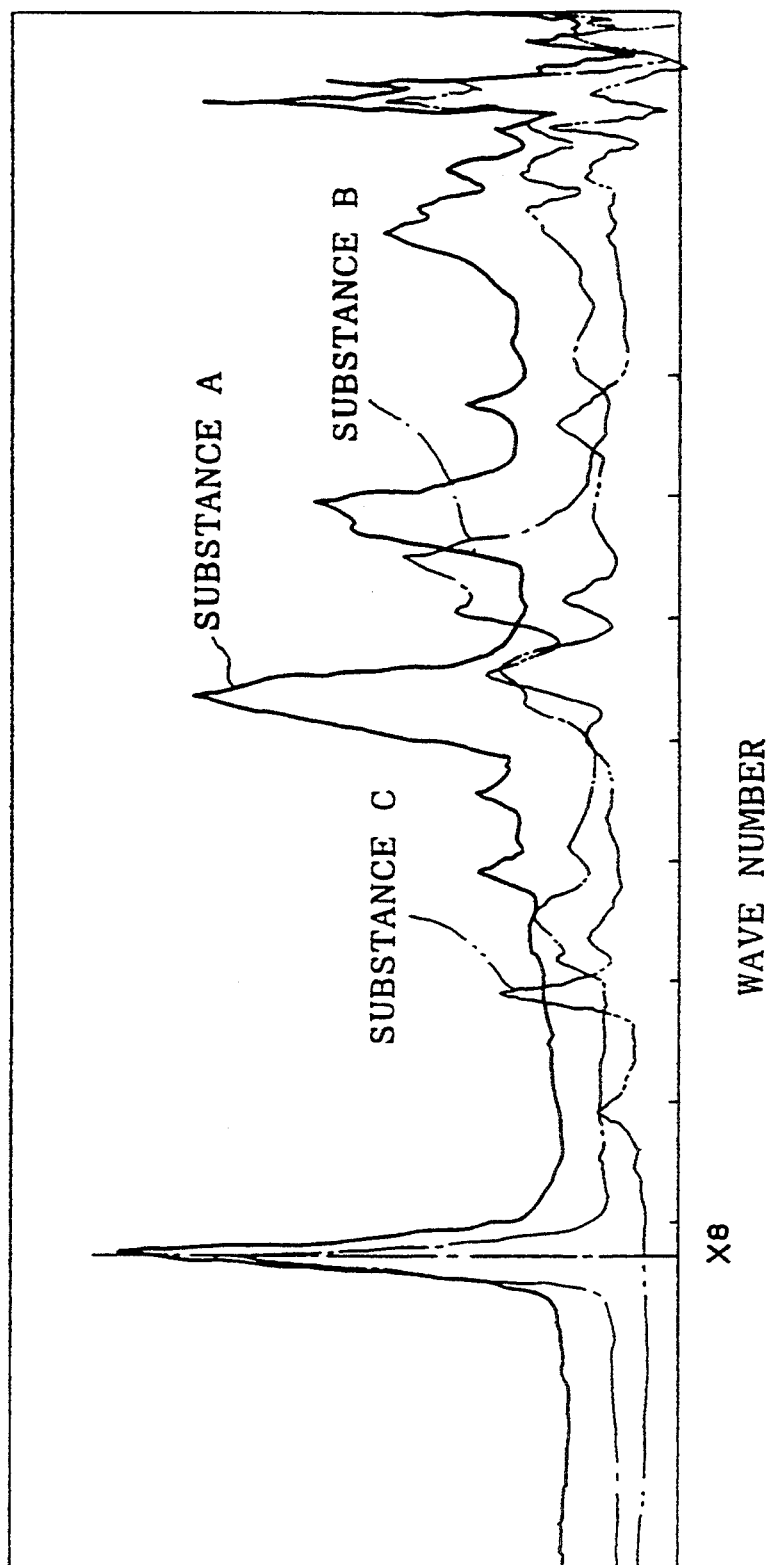

METHOD AND DEVICE FOR ANALYZING SUBSTANCES CONTAINED IN AN AREA

TECHNICAL FIELD

The present invention relates to a method for analyzing an area and a device for analyzing an area, to which the method for analyzing an area is applied.

BACKGROUND INVENTION

Generally, when an organic substance is analyzed to determine the composition of a functional group, infrared radiation is radiated onto the substance. The infrared radiation which has penetrated through the substance or has been reflected from the substance is resolved into spectrums. The infrared intensity for each predetermined wavelength is measured to obtain the spectrum. The infrared wavelength, in which the intensity of absorbing the projected infrared radiation is at its maximum, is respectively different for each functional group. Therefore, the spectrum obtained by measuring the intensity of infrared radiation, which has penetrated through or has been reflected from the substance, generates a peak in its wave form (a maximum value or a minimum value), in accordance with the functional group constituting the organic substance. The wavelength of infrared radiation, in which the peak is generated, allows the functional group constituting the substance to be determined.

When synthetic resin parts such as plastics are checked for impurities and are found to contain impurities and the positions and constitutions of the impurities are analyzed, a so-called area analysis is carried out in which the synthetic parts are cut in a plane, the plane is divided into a plurality of small regions, and infrared radiation is projected onto the small regions so as to analyze each small region in a similar manner to the above.

However, even if elements which constitute substances such as synthetic resin are identical to each other, the properties of the respective substances are very different from each other due to a coupling condition of the molecules or the like. Accordingly, when carrying out the above-described analysis, the method in which a wave form representing a spectrum changes, especially a wavelength of infrared radiation and an infrared intensity at a peak of a wave form representing the spectrum has been observed and pattern matching has been carried out with the state in which the wave form representing the spectrum of previously measured standard samples changes, in order to specify the substances. Therefore, in order to minimize errors and obtain an accurate infrared radiation intensity, it is necessary to carry out several measurements and then adopt the average value, so as to improve accuracy, thereby resulting in an increase in the time required for measurement, analysis, and the like.

With the aforementioned in view, a first object of the present invention is to obtain an area analysis method capable of carrying out measurement and analysis in a short period of time.

A second object of the present invention is to obtain an area analysis device capable of carrying out measurement and analysis in a short period of time.

DISCLOSURE OF THE INVENTION

In order to achieve the aforementioned objects, a first aspect of the present invention will now be explained. An area to be analyzed is divided into a large number of small regions. These small regions are measured photometrically in order to obtain the spectrums of the small regions. Plural principal components are extracted from the obtained spectrums of the small regions, and the principal component marks of each of the extracted plural components are computed for each of the small regions. Then, the plural small regions are classified into plural small region groups so that the small regions, whose principal component marks of specified principal components exceed a predetermined value, are included in an identical small region group, and the substances constituting the classified small region groups are analyzed.

In the first aspect of the present invention, preferably, an optimum small region of the optimum principal component marks of the specified principal component is extracted from each of the small region groups, and based on the spectrum of the optimum small region, the substances constituting each group are analyzed.

A second aspect of the present invention comprises a measuring means which divides an area to be analyzed into a large number of small regions and photometrically measures these small regions to obtain the spectrums of the small regions; a computing means which extracts plural principal components from the obtained spectrums of the small regions and computes the principal component marks of the respective plural components for each of the small regions; a classifying means which classifies the plural small regions into plural small region groups so that the small regions, whose principal component marks of specified principal components exceed a predetermined value, are included in an identical small region group; and an analyzing means which analyzes the substances constituting the classified small region groups.

The analyzing means of the second aspect of the present invention, preferably, extracts an optimum small region of the optimum principal component marks of the specified principal component from each of the small region groups, and analyzes the substances constituting the small region groups based on the spectrum of the optimum small regions.

In the first aspect of the present invention, an area to be analyzed is divided into a large number of small regions and these small regions are measured photometrically, to obtain spectrums, and plural principal components are extracted from the obtained spectrums of the small regions, and the principal component marks of each of the extracted plural components are computed for each of the small regions. The principal components represent a portion in which data values are widely scattered, i.e., in the present invention an important feature for specifying the substances constituting the small regions. The spectrum is composed of data representing light intensity or the like for each predetermined wavelength. The principal components are expressed by coefficients (eigenvector) which provide the respective weight to each data. A large weight is given to a wavelength in which data values are widely scattered. When an area to be measured, comprising substance A in which a large peak is generated in the spectrum, e.g., at the wavelength $\lambda_1$, and substance B in which no peak is generated in the spectrum, e.g., at the wavelength $\lambda_1$, is divided into a plurality of small regions, so as to obtain the spectrums of the small regions, in comparison between the spectrums of the small regions, data values at the wavelength $\lambda_1$ are widely scattered. Thus, the value of data at the wavelength $\lambda_1$ in which the values are extensively scattered, is the important feature for specifying the substances. The principal components extracted in the aforementioned case are expressed by means of coefficients such that a weighting of the data can be increased at the wavelength $\lambda_1$. Accordingly, the principal component marks of the respective principal components, which are computed based on the coefficients, are greatly different between one small region constituted by substance A and another small region constituted by substance B. Therefore, it is determined whether the principal component scores of the respective small regions exceed a predetermined value or not respectively, and when the plural small regions are so classified into plural small region groups that the small regions, whose principal component marks of specified principal components exceed a predetermined value, are included in an identical small region group, it can be determined that the small regions constituting the specified small region groups be constituted by identical substances, and the substances constituting the respective small regions can be respectively specified by analyzing the substances constituting the small region groups.

Further, even if there are plural places in which data values are widely scattered, respectively, it is possible to represent the plural places of scattering by one principal component. Therefore, the feature of the spectrum of a synthetic resin product and the like, which is constituted by a large number of peaks, can be represented by a small number of principal components. In this manner, the principal components are determined in accordance with the extent of scattering of the data, and any high accuracy in the value of the respective data is not required. Even if, for example, values of light intensity to be measured are somewhat scattered due to errors, a scattering of values due to plural peaks occurring at the specified wavelength is, i.e., in comparison between the principal components, sufficiently small, thereby not causing the analyzed results to be largely affected. Accordingly, it is not necessary to obtain the spectrums plural times to improve precision in measurement of light intensity at peaks or the like of the spectrums, thereby allowing the time required for measurement, analysis, and the like, to be shortened.

In the first aspect of the present invention, an optimum small region of the optimum principal component marks of the specified principal component is extracted from each of the small region groups, and the analysis of the substances constituting each group is preferably performed based on the spectrum of the optimum small region. It can be judged that the spectrum of which principal component scores of specified principal components are highest or the spectrum of a central small region, remarkably have the feature that the specified principal components exhibit. Therefore, it is possible to easily specify the substances by the above-described spectrums.

In the second aspect of the present invention, an area to be analyzed is divided into a large number of small regions and these small regions are photometrically measured in order to obtain the spectrums, and plural principal components are extracted from the obtained spectrums of the respective small regions, and the principal component marks of the respective plural components are computed for each of the small regions. Thereby, the plural principal components in which a large weight is imposed on the wavelength in which data values are widely scattered, are extracted from the spectrums of the respective small regions. The small regions which are respectively constituted by different substances are different from each other in the principal component marks of specified principal components. Therefore, it is determined whether the principal component scores of the respective small regions exceed a predetermined value or not respectively, and when the plural small regions are so classified into plural small region groups that the small regions, whose principal component marks of specified principal components exceed a predetermined value, are included in an identical small region group, it can be determined that the small region constituting the specified group be constituted by identical substances, and the substances constituting the respective small regions can be respectively specified by analyzing the substances constituting the respective small region groups. Further, since the principal components are determined in accordance with the extent of scattering of data and any high accuracy in values of the respective data is not required, it is not necessary to obtain the spectrums a plurality of times to improve precision in measurement of light intensity at peaks or like of the spectrums, thereby allowing the time required for measurement, analysis, and the like, to be shortened.

In the second aspect of the present invention, the analyzing means preferably extracts a small region in which principal component marks of the specified principal component is highest or a central small region from the respective small region groups and analyzes the substances constituting the small region groups based on the spectrum of the small region. It can be judged that the spectrum of which principal component marks of specified principal components are highest or the spectrum of a central small region, remarkably have the feature that the specified principal components exhibit. Therefore, it is possible to easily specify the substances by the above-described spectrums.

With the above-described construction of the present invention, the spectrums can be obtained by projecting infrared radiation onto an area to be analyzed. Further, it is possible to obtain the spectrums by projecting visible light onto an area to be analyzed by using Raman scattering.

As explained above, the first and the second aspects of the present invention can obtain an excellent effect in that it is possible to perform measurement and analysis in a short time, since the area to be analyzed is divided into a large number of small regions, and these small regions are photometrically measured so as to obtain the spectrums of the small regions. In addition, plural principal components are extracted from the spectrums of the small regions, and the principal component marks of the respective plural components are computed for each of the small regions. Then, the plural small regions are classified into plural small region groups so that the small regions, whose principal component marks of specified principal components exceed a predetermined value, are included in an identical small region group, so that the substances constituting the small region groups may be analyzed.

BRIEF DESCRIPTION OF THE DRAWINGS

FIG. 6 is a line diagram for illustrating a function of principal component analysis.

BEST EMBODIMENTS FOR CARRYING OUT THE PRESENT INVENTION

Figure 1:
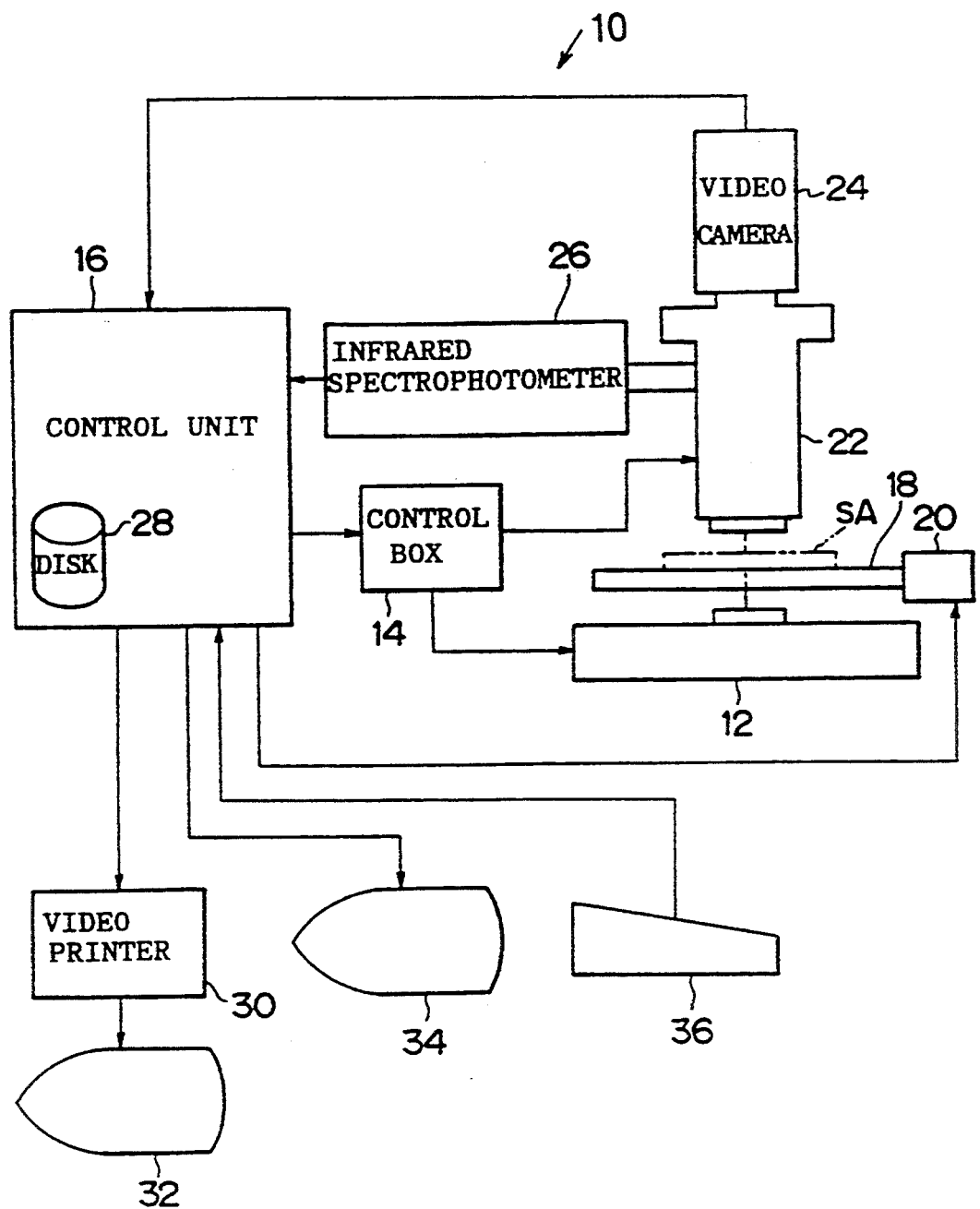
FIG. 1 is a schematic block diagram of an infrared area analysis device according to the present invention.

Referring to the attached drawings, the embodiment of the present invention will be described hereinafter. In FIG. 1, there is shown an infrared area analysis device 10 according to the present embodiment. Rather than a wavelength, the infrared area analysis device 10 employs a wave number (a reciprocal of a wavelength) as a fundamental unit. The infrared area analysis device 10 is provided with an infrared radiation generator 12 which emits infrared radiation having a predetermined wave number. The infrared radiation generator 12 is connected to a control unit 16 via a control box 14, and emits infrared radiation in accordance with instructions from the control unit 16.

Above the infrared radiation generator 12, an XY table 18 is disposed on which a sample to be analyzed SA is placed. The XY table 18 is light-transmissive, and the sample to be analyzed SA which is placed on the XY table 18 is cut thin so as to facilitate transmission of infrared radiation. Thus, infrared radiation emitted from the infrared radiation generator 12 is transmitted through the XY table 18 and the sample to be analyzed SA. The XY table 18 is coupled to the driving portion 20 and is movable in the X direction and Y direction, i.e., two-dimensionally, by the driving portion 20. The driving portion 20 is connected with the control unit 16, and moves the XY table 18 in accordance with an instruction from the control unit 16. Above the XY table 18, a lens barrel 22 is provided in which a diaphragm, a polarizer, and the like (not shown) are accommodated. The infrared radiation which has penetrated through the XY table 18 and the sample to be analyzed SA is made incident within the lens barrel 22. The lens barrel 22 is connected to the control unit 16 via the control box 14. The control unit 16 controls an operation of the diaphragm and the like. A video camera 24 with image-pickup elements such as CCDs is mounted on the infrared radiation output side of the lens barrel 22. The video camera 24, which is connected to the control unit 16, receives the infrared radiation which has penetrated through the sample to be analyzed SA and has passed through the lens barrel 22, and outputs a video signal representing the image of the sample to be analyzed SA to the control unit 16.

In addition, an infrared spectrophotometer 26 is mounted on the lens barrel 22. The lens barrel 22 emits one portion of the incident infrared radiation to the infrared spectrophotometer 26. The infrared spectrophotometer 26 is provided with a spectroscope (not shown) which spectrally resolves the infrared radiation incident from the lens barrel 22, and a photometer (not shown) which measures the intensity of the resolved infrared radiation. The infrared spectrophotometer 26 is connected to the control unit 16, and a band of wave-numbers to be measured and a step width of wave-numbers to be measured of the spectrum are indicated by the control unit 16. The band of wave-numbers to be measured indicates a range of wave-numbers of infrared radiation to be measured, and the step width of wave-numbers to be measured indicates that the infrared radiation is measured at particular degrees of wave-number width within the band of wave-numbers to be measured. The infrared spectrophotometer 26 measures the infrared radiation intensity in accordance with the indicated band of wave-numbers to be measured and the step width of wave-numbers To be measured, and outputs the measured data which represent the spectrum to the control unit 16.

The control unit 16 is provided with a magnetic disk 28. The measured results inputted from the infrared spectrophotometer 26 are stored in the magnetic disk 28. A display 32 is connected to the control unit 16 via a video printer 30. The control unit 16 outputs a video signal and the like, which are outputted from the video camera 24, to the display 32 via the video printer 30. Thus, the display 32 represents the image of the sample to be analyzed SA. Further, based on the inputted video signal, the video printer 30 prints, if required, the image of the sample to be analyzed SA. In addition, the display 34 is also connected to the control unit 16. The control unit 16 allows the display 34 to represent information concerning the analyzed results and the like. A keyboard 36 for inputting data and the like is also connected to the control unit 16.

Figure 2:
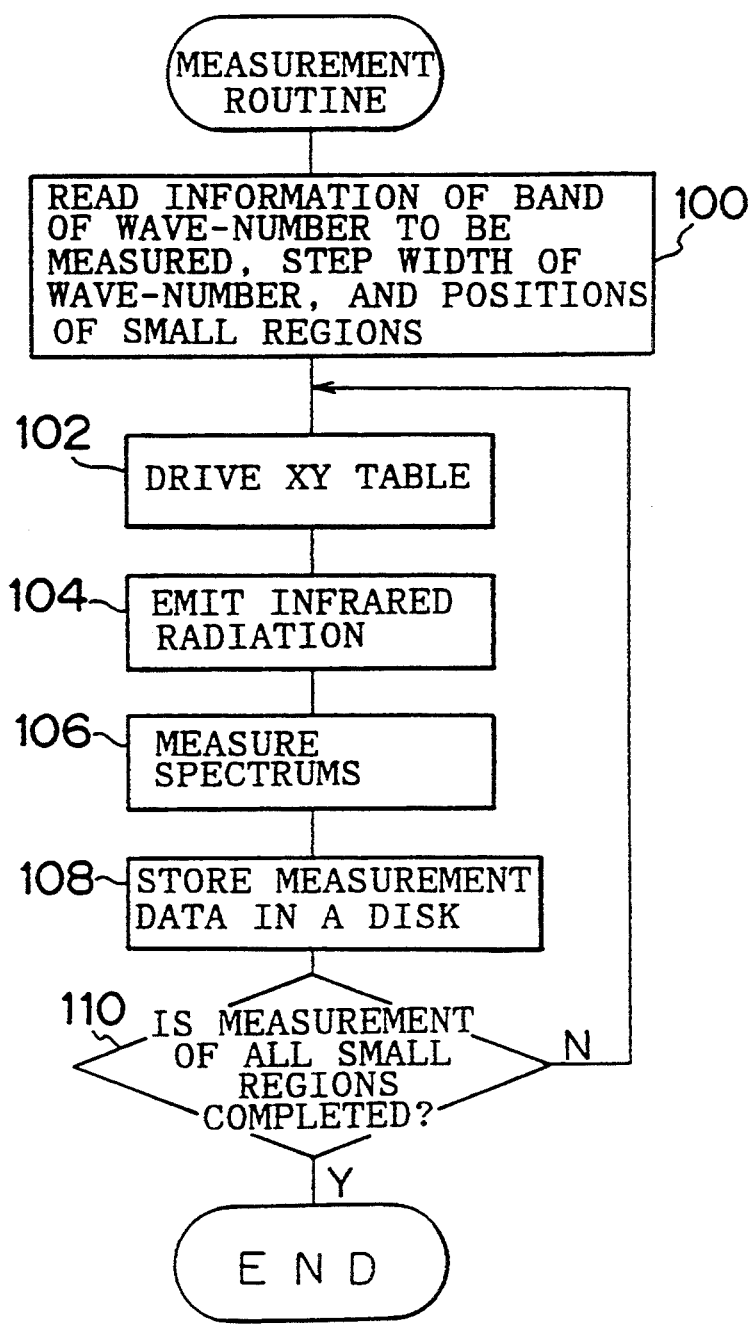
FIG. 2 is a flow chart illustrating a measuring process for each small region of the present invention.

Next, the operation of the present embodiment will be described. Referring to the flow chart of FIG. 2, a measuring process of the sample to be analyzed is first explained.

Figure 4:
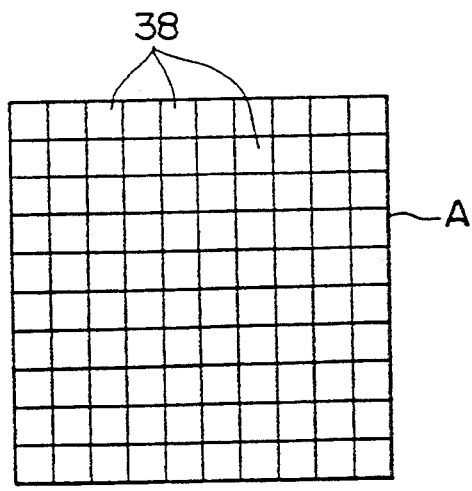
FIG. 4 is a diagram illustrating the concept of small regions.

In a step 100, information of the band of wave-numbers to be measured, the step width of wave-numbers, and the like of the spectrum, being previously stored in the magnetic disk 28 or the like, is read out. In the present embodiment, the band of wave-number to be measured is set to be in the range from 1,000 to 2,000 cm$^{-1}$ (a wavelength of 5,000 to 10,000 nm) in which there is a little influence of moisture, carbonic acid gas, and the like. The step width of wave-numbers is set to be, e.g., about 4 to 16 cm$^{-1}$. Further, the infrared area analysis device 10 divides an analyzed area of the sample to be analyzed SA into, for example, 10×10 small regions 38 as shown in FIG. 4, or 30×30 small regions, or the like, in order to perform measurements for the respective small regions. Therefore, information about positions (coordinates) of the respective small regions, is also read out.

In a step 102, based on the information about the positions of the small regions, the XY table 18 is moved so that infrared radiation is projected onto a small region to be first measured. In a step 104, infrared radiation is emitted from the infrared radiation generator 12. The infrared radiation emitted from the infrared radiation generator 12 penetrates through the XY table 18 and the small region which is first measured of the sample to be analyzed SA, and one portion of the infrared radiation is made incident into the infrared spectrophotometer 26 and is spectrally resolved. The remaining portion thereof is made incident into the video camera 24.

In a step 106, the band of wave-numbers to be measured and the step width of wave-numbers of the spectrum are indicated to the infrared spectrophotometer 26 and simultaneously the infrared spectrophotometer 26 starts measuring the infrared radiation. Thereby, the infrared spectrophotometer 26 starts measuring the infrared radiation of which the intensity is larger than that having, e.g., the wave number of 2,000 cm$^{-1}$ at one end of the band of wave-numbers to be measured, and measures the intensity of the infrared radiation to the other end of the band of wave-number to be measured up to, e.g., the wave number of 1,000 cm$^{-1}$ for each step width of wave-number The measurement data is outputted to the control unit 16. When the infrared spectrophotometer 26 measures the intensity of the infrared radiation to the other end of the band of wave-number to be measured up to the wave number of 1,000 cm$^{-1}$, measuring the spectrum for one small region is completed. In the next step 108, the input measurement data is stored in the magnetic disk 28.

The next step 110 determines whether the measuring process for all of the small regions has been completed or not. If the decision at the step 110 is no, in the step 102 the XY table 18 is driven so that infrared radiation may be projected onto the small region to be measured next. Then, in steps 104 through 110 a measuring process is performed in the same manner as that aforementioned. In this way, the measuring process is performed on all of the small regions by projecting infrared radiation onto the respective small regions successively. When the decision at step 110 is yes, the measuring process is completed.

In the above-described process, when the intensity of infrared radiation of the wave numbers of p kinds are measured for the respective n small regions, the measurement data $X_{11}, \ldots, X_{pn}$, as shown in the following table 1, are obtained. These measurement data are stored in the magnetic disk 28. The respective small regions are, for convenience sake, numbered as small region numbers 1, 2, 3 ... n so that they may be distinguished from each other. Further, the measurement data of the respective small region, e.g., the measurement data $(X_{11}, X_{21}, X_{31}, \ldots, X_{p1})$ of the small region numbered as 1 represents the spectrum of this small region 1.

TABLE 1

| SMALL REGION NUMBER | WAVE NUMBERS | | | | |
|---|---|---|---|---|---|
| | $X_1$ | $X_2$ | $X_3$ | ... | $X_p$ |
| 1 | $X_{11}$ | $X_{21}$ | $X_{31}$ | | $X_{p1}$ |
| 2 | $X_{12}$ | $X_{22}$ | $X_{32}$ | | $X_{p2}$ |
| 3 | $X_{13}$ | $X_{23}$ | $X_{33}$ | | $X_{p3}$ |
| 4 | $X_{14}$ | $X_{24}$ | $X_{34}$ | | $X_{p4}$ |
| : | : | : | : | | : |
| n | $X_{1n}$ | $X_{2n}$ | $X_{3n}$ | | $X_{pn}$ |

Figure 3:
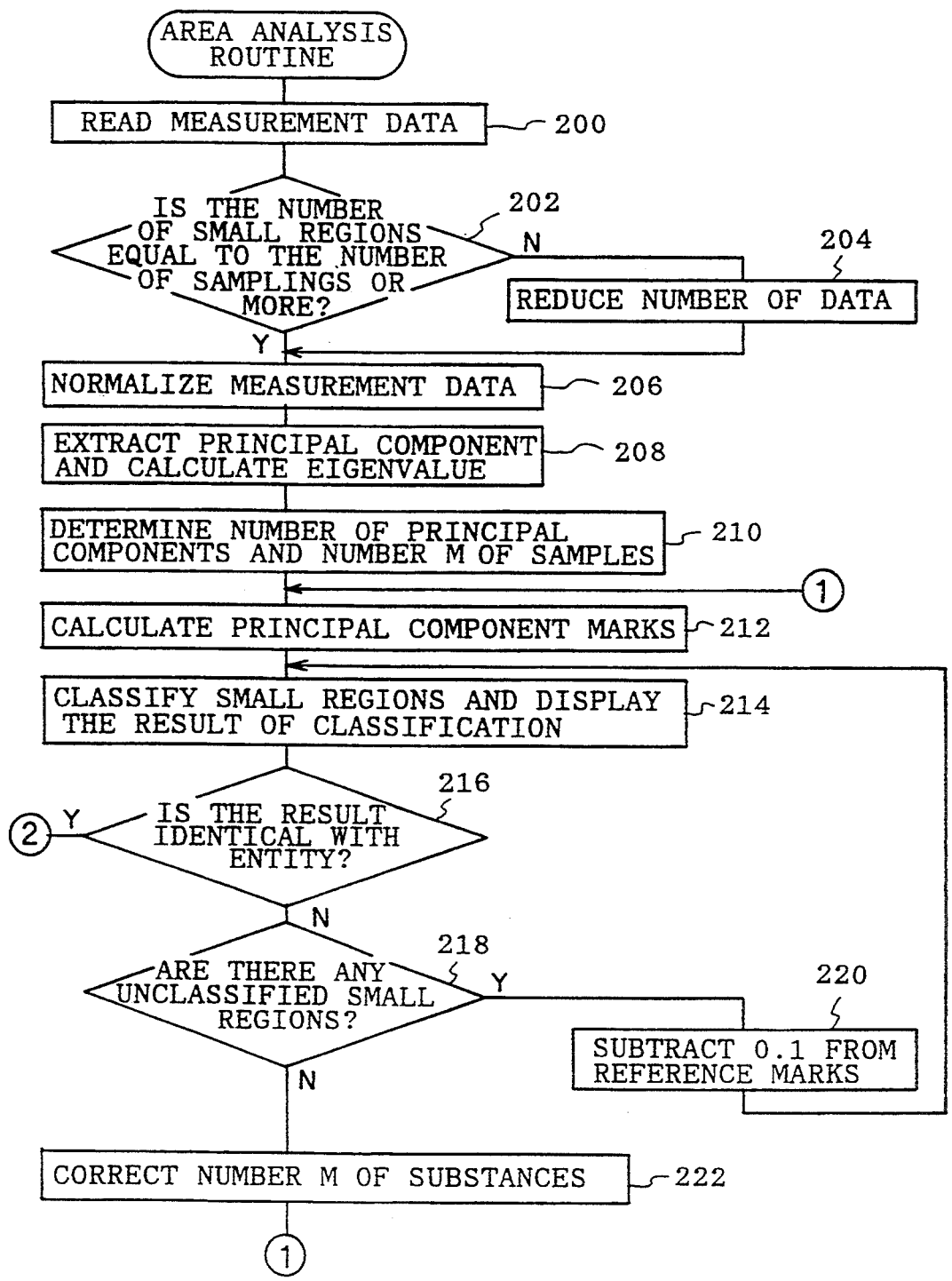
FIG. 3 is a flow chart illustrating an area analysis process of the present invention.
Figure 3:
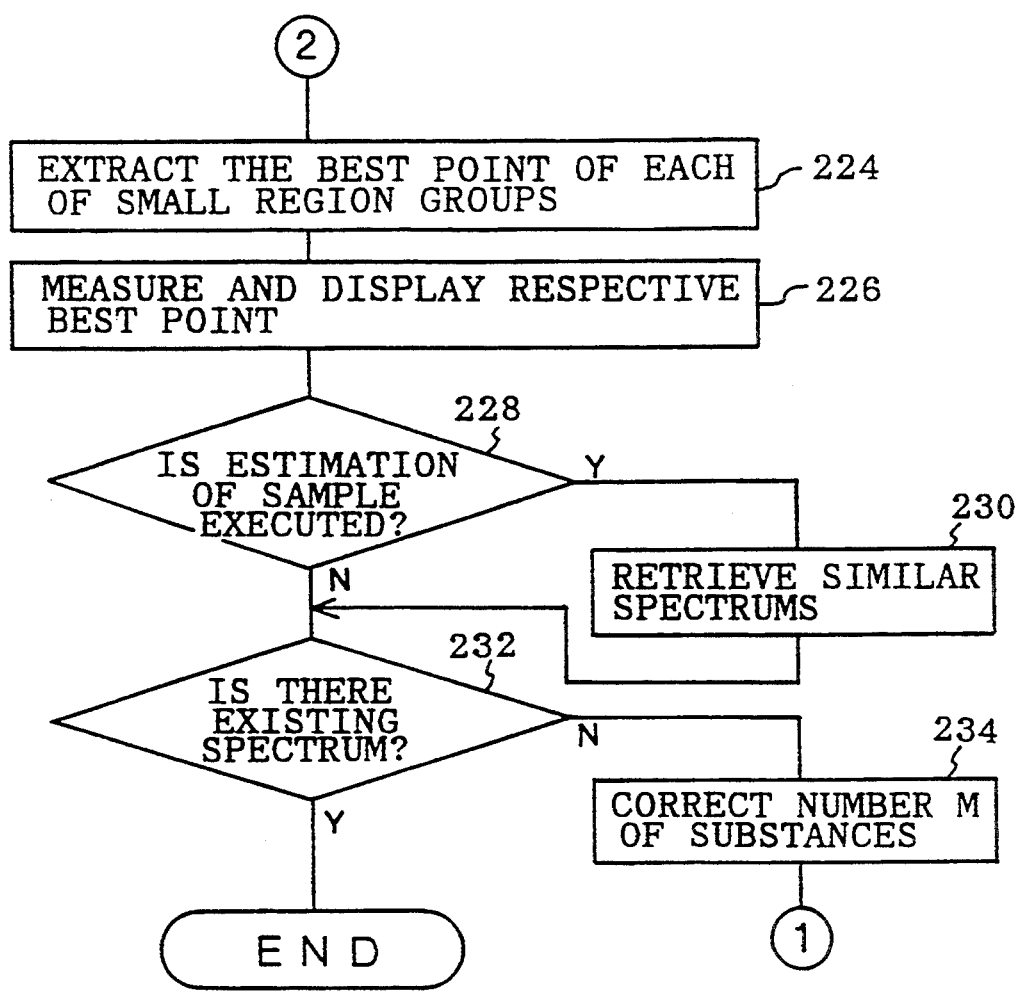

Next, based on the measurement data obtained by the above-described measuring process, a process for area analysis on the sample to be analyzed SA, is explained with reference to the flow chart of FIG. 3. In step 200, the measurement data as shown in Table 1, which have been stored in the magnetic disk 28, are read in. Step 202 determines whether the number n of small regions Is equal to the number of samplings, p, or more. When the decision at the step 202 is no, the process proceeds to step 204.

When principal components are extracted by a principal component extracting process as described below, from the measurement data which have been obtained by measuring the intensity of infrared radiation having the wave numbers of p kinds for the respective n small regions, when there is little data, i.e., n<p, it is not possible to obtain any solution of an eigenvalue, and in step 204 the number of data is reduced. For example, peaks of values of measurement data for the respective small regions are obtained, and measurement data of predetermined wave numbers of which values of measurement data for all the small regions do not come to a peak, i.e., photometric data of which values are less than the peak, are eliminated. Since the principal components extracted from the measurement data impose a large weight on a variable (wave number) in which the measurement data are extensively scattered, e.g., the wave number of which a value of measurement data comes to a peak in one small region and of which a value of measurement data is less than a peak in another small region, they are not greatly influenced even if the data of a predetermined wave number less than a peak in all the small regions are eliminated.

In the next step 206, normalization for varying the values of the respective measurement data is carried out so that the average value of the measurement data is 0 and the value of distribution thereof is 1. Thereby, influences from the state of an area to be analyzed. e.g., the scattering of light transmission, are eliminated. Step 208 extracts principal components. The principal components are extracted by carrying out, e.g., a computation as described below.

When p variables (wave numbers in the present embodiment) are measured for the respective n fields (the respective small regions in the present embodiment), a composite variable, z is considered which is expressed by the following formula (1) with p variables, $X_1, X_2, \ldots, X_p$ is used.

$$z = a_1 X_1 + a_2 X_2 + \ldots + a_p X_p = \sum_{j=1}^{p} a_j X_j \quad (1)$$

The distribution V(z) of the composite variable z is expressed in the following formula (2).

$$V(z) = \frac{1}{n} \sum_{i=1}^{n} \{a_1(X_{1i} - \bar{X}_1) + \ldots + a_p(X_{pi} - \bar{X}_p)\}^2 \quad (2)$$

Extraction of the principal components corresponds to maximizing the distribution of the composite variables. Thus, coefficients $a_{11}, \ldots, a_{pp}$, and fixed values $\lambda_1, \ldots, \lambda_p$ are computed which represent p principal components as shown in the following table 2. A description about the deriving process of the principal components will be omitted.

TABLE 2

| VARIABLE (VARIATE) | COEFFICIENT OF 1ST PRIN. COMP. | COEFFICIENT OF 2ND PRIN. COMP. | COEFFICIENT OF 3RD PRIN.COMP. | ... | COEFFICIENT OF pTH PRIN. COMP. |
|---|---|---|---|---|---|
| $X_1$ | $a_{11}$ | $a_{12}$ | $a_{13}$ | ... | $a_{p1}$ |
| $X_2$ | $a_{21}$ | $a_{22}$ | $a_{23}$ | ... | $a_{p2}$ |
| $X_3$ | $a_{31}$ | $a_{32}$ | $a_{33}$ | ... | $a_{p3}$ |

TABLE 2-continued

| VARIABLE (VARIATE) | COEFFICIENT OF 1ST PRIN. COMP. | COEFFICIENT OF 2ND PRIN. COMP. | COEFFICIENT OF 3RD PRIN.COMP. | ... | COEFFICIENT OF pTH PRIN. COMP. |
|---|---|---|---|---|---|
| : | : | : | : | | : |
| : | : | : | : | | : |
| $X_p$ | $a_{p1}$ | $a_{p2}$ | $a_{p3}$ | ... | $a_{pp}$ |
| EIGEN-VALUES | $\lambda_1$ | $\lambda_2$ | $\lambda_3$ | ... | $\lambda_p$ |

The relationship between the respective eigenvalues is as follows:

$$\lambda_1 \geq \lambda_2 \geq \ldots \geq \lambda_p \geq 0 \quad (3)$$

The first principal component corresponding to the maximum eigenvalue $\lambda_1$ is expressed by composite variables described below, in which elements of eigenvectors ($a_{11}, \ldots, a_{pp}$) are coefficients.

$$z_1 = a_{11}X_1 + a_{21}X_2 + \ldots + a_{p1}X_p \quad (4)$$

In the same manner, the second and subsequent principal components are respectively represented as follows.

$$\begin{aligned} z_2 &= a_{12}X_1 + a_{22}X_2 + \ldots + a_{p2}X_p \\ z_3 &= a_{13}X_1 + a_{23}X_2 + \ldots + a_{p3}X_p \\ &\vdots \\ z_p &= a_{1p}X_1 + a_{2p}X_2 + \ldots + a_{pp}X_p \end{aligned} \quad (5)$$

As will be obviously seen from the above-described formulas (4) and (5), the eigenvectors ($a_{11}, \ldots, a_{pp}$) are coefficients for weighting each of the composite variables $z_1, \ldots, z_p$. When, for example, the sample to be analyzed SA is constituted by three kinds of substances A, B, and C having respective spectrums as shown in FIG. 6, and the distribution of measurement data of the respective variables, i.e., the respective wave numbers, is maximum at the wave number $X_8$, the value of the eigenvector $a_{81}$ of the first principal component is increased. The measurement data at the time the infrared radiation of wave number $X_8$ is projected, is given a large weight. Therefore, the substances A and B which have respective peaks of infrared radiation intensity at the wave number $X_8$ are greatly different from the substance C with no peak generated, in the composite variable $Z_1$ of the first principal component, i.e., the value of principal component marks which will be described below. Due to the difference in tills value, it is possible to easily classify substances.

Further, as described above, the principal components are dependent upon the distribution of the measurement data at the respective wave numbers. High accuracy is not required for values of the measurement data of the respective small regions. Accordingly, it is not necessary to perform plural measurements as in the conventional method for computing an average value to improve precision in measurement of the intensity of infrared radiation at a peak and the like. It is also possible to shorten the time required for analysis due to a reduced time for measurement and reduced data volume.

Step 210 determines the number D of principal components, and the number M of substances, which indicates the number of substances constituting an area to be analyzed. The number D of principal components is a number of principal components employed in a process such as classification in the next step 212 and in subsequent steps. The principal components in which the eigenvalue $\lambda$ can satisfy the following expression (6) are employed.

$$\lambda_m \geq \frac{\sqrt{p}}{2} \quad (6)$$

(wherein, $m = 1, \ldots, p$)

The above expression (6) is an empirical expression obtained from experiments carried out by the inventor of the present invention. The principal components which do not satisfy the expression (6) have eigenvalues $\lambda$ that are lowered, and the ratio of principal components to the entire distribution of an original variable, the so-called contributive rate, is low. Therefore, there is little influence on a process such as classification in the next step 212 and in subsequent steps. Also, there is no possibility of a problem occurring even if they are not employed as principal components in a process such as classification. Further, since it is possible to analyze the same number of substances as that of the employed principal components, the step 210 establishes the same value as the number D of the principal component, assuming that the number of substances is M.

Step 212 computes the principal component marks of the respective principal components for each of the small regions. The principal component marks are the values of the principal components $z_1, \ldots z_p$ which are computed by substituting measurement data $X_{11}, X_{21}, X_{31}, \ldots X_{p1}$ for variables $X_1, X_2, \ldots, X_p$ in the formulas (4) and (5). However, only the principal component marks of the principal components which are employed in step 210 are computed for each of the small regions. For example, if the number of principal components D equals three, the principal component marks $z_{11}, \ldots, z_{3n}$ of the first to the third principal components are computed for each of the small regions.

TABLE 3

| SMALL REGION NUMBER | 1ST PRIN. COMPONENT | 2ND PRIN. COMPONENT | 3RD PRIN. COMPONENT |
|---|---|---|---|
| 1 | $z_{11}$ | $z_{21}$ | $z_{31}$ |
| 2 | $z_{12}$ | $z_{22}$ | $z_{32}$ |
| 3 | $z_{13}$ | $z_{23}$ | $z_{33}$ |
| : | : | : | : |
| : | : | : | : |
| n | $z_{1n}$ | $z_{2n}$ | $z_{3n}$ |

The principal component marks respectively represent the relationship between each data (measurement data of the respective small region in the present embodiment) and each principal component. For example, a small region in which the principal component marks of the first principal is highest or a central small region has remarkably the feature represented by the first principal component, and it can be determined that the first principal component generates a peak at the wave number in which a large weight is given. Therefore, if classified based on the magnitude of the principal component marks, it can be determined that the small regions classified into an identical small region group are constituted by identical substances.

Figure 5A:
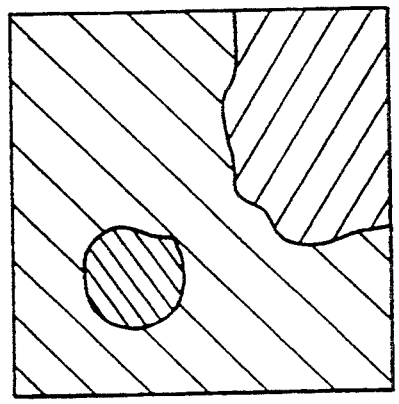
FIG. 5A is a schematic diagram showing an example of an image of an area to be analyzed.
Figure 5B:
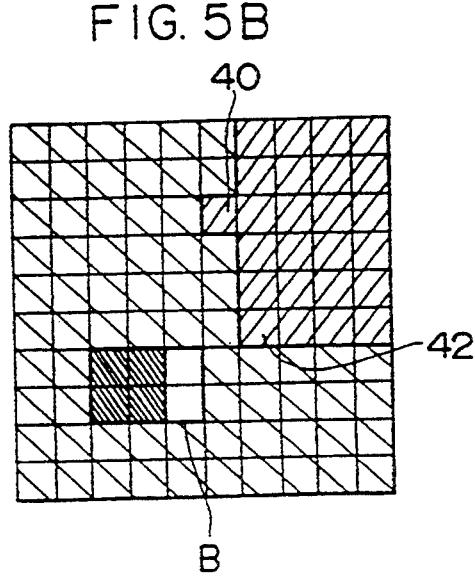
FIG. 5B is a schematic diagram showing an example in which a classified result is displayed.

Step 214 classifies the respective small region based on the principal component marks. In this classification method, it is determined whether, for example, the principal component marks $z_{11}, \ldots, z_{1n}$ of the first principal component of the respective small regions exceed a reference score (e.g., 1) or not, and then the small region, whose principal component marks exceed a reference score, is classified as a small region which corresponds to the first principal component. Next, it is determined whether, the principal component marks $z_{21}, \ldots, z_{2n}$ of the second principal component of the small regions which have not been classified into the first principal component, exceed a reference value or not. They are then classified in the same manner as above. Further, it is determined whether, the principal component marks $z_{31}, \ldots, z_{3n}$ of the third principal component of the small regions which have not been classified into the second principal component, exceed a reference value or not. They are also then classified in the same manner as above. In case of the number of principal components exceeding three, the small regions are also classified in the same manner. In the present embodiment, an initial value of reference marks is one. When the classification is completed, the classified results are represented in the display 34, as shown in FIG. 5B. The classified results are the actual image of an area to be analyzed, and are represented with the same color for each of the classified small region groups. Unclassified small regions (for example, the region B of FIG. 5B) of which no principal component marks exceeds the reference marks in the above-described classification process are represented with no coloring.

Step 216 determines whether the classified results are identical with the entity or not. An operator of the infrared area analysis device 10 makes a comparison between the image of an area to be analyzed of the sample to be analyzed SA represented in the display 32 as shown in FIG. 5A, and the classified results represented in the display 34 as shown in FIG. 5B and determines whether or not, for example, the classified results correspond to the actual color distribution of the area to be analyzed, and then inputs the determined results by operating a key board 36. For example, assuming that it is determined that, in FIG. 5B, a small region 40 and a small region 42 do not correspond to the real object, in such a case the determined results that they do not correspond to the entity, are inputted. If the determined results that they do not correspond to the entity are inputted, the process proceeds to step 218 where it is determined whether any unclassified small regions which are represented with no coloring exist or not, if the decision in step 218 is yes, step 220 subtracts 0.1 from the reference marks, and the process is returned to step 214. Thus, classification criteria is lowered, so as to carry out re-classification. If the decision at step 218 is no, the number D of the principal components and the values of the number M of the substances are corrected so as to correspond to the entity. The process then returns to step 212. Then, the processes in steps 212 through 222 are repeated until the decision at the step 216 is yes.

Figure 7:
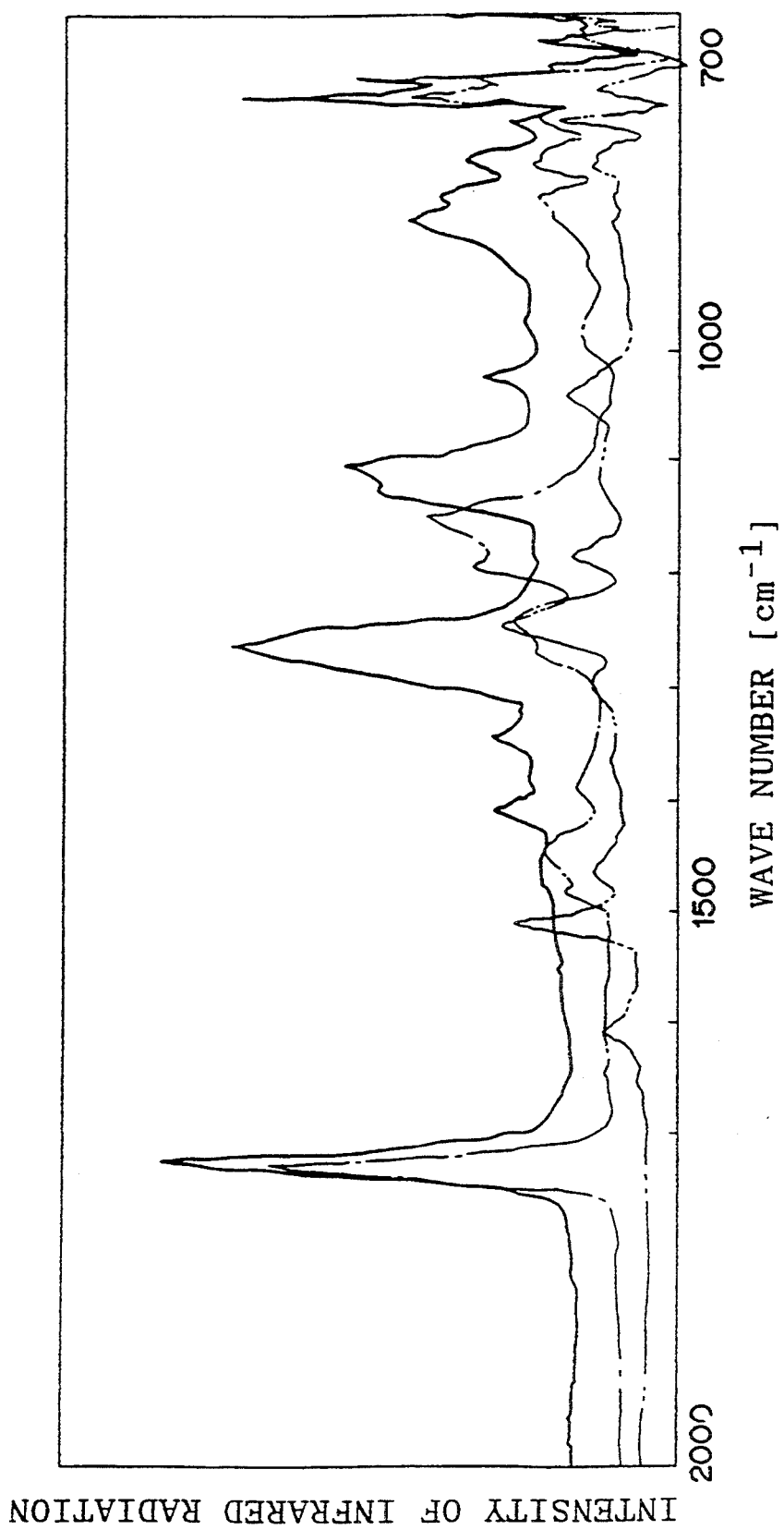
FIG. 7 is a line diagram showing an example in which a measured result of the best point is displayed.

If the decision at step 216 is yes, the process proceeds to step 224, and the best point which is the small region of the highest principal component marks among the respective small region groups classified that are constituted by an identical substance, is extracted from each of the small region groups. In step 226, in the same way as the measuring process of the flow chart in FIG. 2, infrared radiation is projected onto the respective small regions which have been extracted as the best point from each of the small region groups. The intensity of infrared radiation is measured by varying the wave numbers of infrared radiation. This allows the spectrums for the respective best points to be obtained as shown in FIG. 7, and the spectrums are represented in the display 34.

Next, step 228 determines whether estimation (identification) of the substances constituting the respective best points is executed or not in the infrared area analysis device 10. It requires skill in estimating substances with reference to the displayed spectrums. If an operator of the infrared area analysis device 10 is a skilled worker, the decision at step 228 will be yes. If the operator is unskilled in the estimation of substances, the decision at step 228 will be no. If the decision at step 228 is yes, the process proceeds to step 230, and a similar spectrum is retrieved from the previously-stored spectrums. In this case, since the best point is the small region of the highest principal component marks among each of the small region groups, it is the small region which has the remarkable feature represented by the respective principal components. Accordingly, when the respective principal components represent the feature of substances accurately, it is possible to easily estimate the substances of each best point.

Step 232 determines whether the spectrums of the respective best points measured in step 226 are those of existing substances. If, for example, a similar spectrum does not exist in the process in step 230, or if the substances have not been judged what they are when the substances are estimated by a skilled worker, this decision is made no. When the decision in step 232 is no, it is considered that the principal components do not accurately represent the features of substances constituting the respective small regions, for example, the small region of the best point is constituted by a plurality of substances. Therefore, the values of the number M of substances are corrected in step 234, and the process is returned to step 212. If the decision at step 232 is yes, the process is completed.

In this manner, in the present embodiment, plural principal components of which the respective wavelengths are expressed as variables are extracted, the principal component marks of the plural principal components are computed for each of the small regions, and based on the principal component marks the small regions are respectively classified. Therefore, it is not necessary to perform measurements a plurality of times. It is also unnecessary to improve the precision of measurement of the intensity of infrared radiation at a peak or the like. Further, it is possible to reduce measuring time, and analysis time due to a decreased amount of data.

Although, in the present embodiment, spectrums are obtained by measuring the intensity of infrared radiation which penetrates through the sample to be analyzed SA, it is also possible to obtain the spectrums by measuring the intensity of infrared radiation reflected from the sample to be analyzed SA. Further, the spectrums can be also obtained by projecting visible light on an area to be analyzed and then using Raman scattering.

In addition, although the above-described embodiment is given as an example in which an area to be measured is divided into a large number of small regions and measured photometrically by moving the sample to be analyzed, the present invention is not limited to this example. The area to be measured may be divided into a large number of small regions and may be measured photometrically so as not to move the sample to be analyzed by scanning infrared radiation on the area to be measured by means of a rotating polygon mirror, a galvanometer mirror, and the like.

Further, although the above-described embodiment is given as an example in which a small region of the highest principal component marks or a small region in the center is extracted and analyzed, values of the principal component marks of the small region to be extracted can be determined through experiments, and based on the principal component marks, the small region most suitable for analysis of substances can be extracted and analyzed.

I claim:

1. An area analysis method, comprising the steps of:
    dividing an area to be analyzed into a plurality of small regions and measuring the small regions photometrically to obtain spectrums of the respective small regions;
    extracting a plurality of principal components from said obtained spectrums of the respective small regions;
    computing principal component marks of each of said extracted principal components for each of the small regions;
    classifying the plurality of small regions into a plurality of small region groups so that the small regions whose principal component marks of specified principal components exceed a predetermined value are included in identical ones of the small region groups; and
    determining the substances constituting the classified small region groups based on the principal component marks.

2. An area analysis method according to claim 1, further comprising the step of extracting an optimum principal component mark of said specified principal component from each of said small region groups, wherein the step of determining the substances constituting the small region groups is carried out based on the optimum principal component mark.

3. An area analysis method according to claim 1, wherein an eigenvalue applied as a weighting factor to the principal components satisfies the following expression:

$$\lambda_m \geq \frac{\sqrt{p}}{2}$$

wherein, $m=1, \ldots, p$, and $p$ is a number of data which are measured in the respective small regions.

4. An area analysis device, comprising:
    photometric measuring means for dividing an area to be analyzed into a plurality of small regions and photometrically measuring the small regions to obtain spectrums of the respective small regions;
    computing means for extracting a plurality of principal components from said obtained spectrums of the respective small regions and computing principal component marks of each of said extracted principal components for each of the small regions;
    classifying means for classifying the large number of small regions into a plurality of small region groups so that the small regions whose principal component marks of specified principal components exceed a predetermined value are included in identical ones of the small region groups; and
    determining means for determining the substances constituting the classified small region groups based on the principal component marks.

5. An area analysis device according to claim 4, wherein said analyzing means extracts a representative principal component mark of said specified principal component from each of said small region groups, and determines the substances constituting the small region groups based on the representative principal component mark.

6. An area analysis device, according to claim 4, wherein an eigenvalue applied as a weighting factor to the principal components satisfies the following expression:

$$\lambda_m \geq \frac{\sqrt{p}}{2}$$

wherein, $m=1, \ldots, p$, and $p$ is a number of data which are measured in the respective small regions.

* * * * *